US006976958B2

(12) United States Patent
Quy

(10) Patent No.: US 6,976,958 B2
(45) Date of Patent: Dec. 20, 2005

(54) METHOD AND APPARATUS FOR HEALTH AND DISEASE MANAGEMENT COMBINING PATIENT DATA MONITORING WITH WIRELESS INTERNET CONNECTIVITY

(75) Inventor: Roger J. Quy, Mill Valley, CA (US)

(73) Assignee: Q-Tec Systems LLC, Wilmington, DE (US)

(*) Notice: Subject to any disclaimer, the term of this patent is extended or adjusted under 35 U.S.C. 154(b) by 75 days.

(21) Appl. No.: 10/773,501

(22) Filed: Feb. 6, 2004

(65) Prior Publication Data

US 2004/0162466 A1 Aug. 19, 2004

Related U.S. Application Data

(63) Continuation-in-part of application No. 10/418,845, filed on Apr. 18, 2003, which is a continuation of application No. 09/738,270, filed on Dec. 15, 2000, now Pat. No. 6,602,191.

(51) Int. Cl.[7] .............................. A61B 5/00; H04N 7/06
(52) U.S. Cl. ................. 600/301; 340/539.12; 128/903; 128/904; 725/116
(58) Field of Search ................................. 600/300, 301, 600/345, 365, 481, 483, 485, 509, 529; 607/27, 60, 30–32; 128/903–905, 920; 348/14.01; 725/116, 131; 705/2

(56) References Cited

U.S. PATENT DOCUMENTS

| | | | |
|---|---|---|---|
| 4,282,883 A | | 8/1981 | Yerushalmy |
| 5,012,814 A | | 5/1991 | Mills et al. |
| 5,307,263 A | | 4/1994 | Brown |
| 5,357,427 A | | 10/1994 | Langen et al. |
| 5,434,611 A | * | 7/1995 | Tamura ....................... 725/116 |
| 5,441,047 A | | 8/1995 | David et al. |

(Continued)

FOREIGN PATENT DOCUMENTS

| | | | |
|---|---|---|---|
| JP | 2002344660 A | * 11/2002 | ................. 725/116 |
| WO | WO 95/32480 | 11/1995 | |
| WO | WO 97/28736 | 8/1997 | |
| WO | WO 97/28737 | 8/1997 | |
| WO | WO 98/24358 | 6/1998 | |
| WO | WO 98/38909 | 9/1998 | |
| WO | WO 99/04687 | 2/1999 | |
| WO | WO 99/14882 | 3/1999 | |
| WO | WO 99/41682 | 8/1999 | |
| WO | WO 99/44494 | 9/1999 | |
| WO | WO 99/46718 | 9/1999 | |
| WO | WO 00/36900 | 6/2000 | |
| WO | WO 00/40145 | 7/2000 | |
| WO | WO 00/54205 | 9/2000 | |
| WO | WO 00/54206 | 9/2000 | |
| WO | WO 00/62662 | 10/2000 | |
| WO | WO 01/24038 | 4/2001 | |

OTHER PUBLICATIONS

U.S. Appl. No. 60/264,739, filed Jan. 2001, Posa et al.
Jyrki Oraskari ; "Bluetooth versus WLAN IEEE 802.11x"; Helsinki University of Technology (Department of Computer Science and Engineering) Nov., 2000.

(Continued)

Primary Examiner—Willis R. Wolfe, Jr.
(74) Attorney, Agent, or Firm—Mark D. Wieczorek

(57) ABSTRACT

Embodiments of the invention provide a method and apparatus for a wireless health monitoring system for interactively monitoring a disease or health condition of a patient by connecting an internet-enabled wireless web device ("WWD") to a digital camera or other health monitoring device. The WWD may accommodate a memory device for enhanced storage capabilities that may be particularly pertinent to data-intensive tasks such as the handling and storage of images or other visual data. The health related data is transmitted from the WWD to a server using standard internet protocols and may be integrated with various operating systems for handheld or wireless devices, especially those with enhanced capabilities for handing images and visual data.

17 Claims, 12 Drawing Sheets

U.S. PATENT DOCUMENTS

| | | | |
|---|---|---|---|
| 5,544,649 A * | 8/1996 | David et al. ................. | 600/301 |
| 5,544,661 A | 8/1996 | Davis et al. | |
| 5,549,117 A | 8/1996 | Tacklind et al. | |
| 5,553,609 A * | 9/1996 | Chen et al. ................. | 600/301 |
| 5,601,435 A | 2/1997 | Quy | |
| 5,626,144 A | 5/1997 | Tacklind et al. | |
| 5,678,562 A | 10/1997 | Sellers | |
| 5,701,904 A | 12/1997 | Simmons et al. | |
| 5,704,366 A | 1/1998 | Tacklind et al. | |
| 5,724,025 A | 3/1998 | Tavori | |
| 5,732,709 A | 3/1998 | Tacklind et al. | |
| 5,735,285 A | 4/1998 | Albert et al. | |
| 5,752,917 A | 5/1998 | Fuchs | |
| 5,772,586 A | 6/1998 | Heinonen et al. | |
| 5,791,342 A | 8/1998 | Woodard | |
| 5,931,791 A | 8/1999 | Saltzstein et al. | |
| 5,933,136 A | 8/1999 | Brown | |
| 5,935,060 A | 8/1999 | Iliff | |
| 5,941,829 A | 8/1999 | Saltzstein et al. | |
| 5,951,300 A | 9/1999 | Brown | |
| 5,959,533 A | 9/1999 | Layson et al. | |
| 5,964,701 A | 10/1999 | Asada et al. | |
| 5,967,975 A | 10/1999 | Ridgeway | |
| 5,987,352 A | 11/1999 | Klein et al. | |
| 5,987,519 A | 11/1999 | Peifer et al. | |
| 5,997,476 A | 12/1999 | Brown | |
| 6,022,315 A | 2/2000 | Iliff | |
| 6,024,699 A | 2/2000 | Surwit et al. | |
| 6,050,940 A | 4/2000 | Braun et al. | |
| 6,055,506 A | 4/2000 | Frasca, Jr. | |
| 6,057,758 A | 5/2000 | Dempsey et al. | |
| 6,059,692 A | 5/2000 | Hickman | |
| 6,083,156 A | 7/2000 | Leseicki | |
| 6,101,478 A | 8/2000 | Brown | |
| 6,144,837 A | 11/2000 | Quy | |
| 6,160,478 A | 12/2000 | Jacobsen et al. | |
| 6,168,563 B1 | 1/2001 | Brown | |
| 6,190,324 B1 | 2/2001 | Kieval et al. | |
| 6,266,645 B1 | 7/2001 | Simpson | |
| 6,319,199 B1 | 11/2001 | Sheehan et al. | |
| 6,336,900 B1 | 1/2002 | Alleckson et al. | |
| 6,375,614 B1 | 4/2002 | Braun et al. | |
| 6,386,882 B1 | 5/2002 | Lindberg | |
| 6,416,471 B1 | 7/2002 | Kumar et al. | |
| 6,418,346 B1 * | 7/2002 | Nelson et al. ................. | 607/30 |
| 6,440,068 B1 | 8/2002 | Brown et al. | |
| 6,450,955 B1 | 9/2002 | Brown et al. | |
| 6,458,080 B1 | 10/2002 | Brown et al. | |
| 6,529,771 B1 | 3/2003 | Kieval et al. | |
| 6,602,191 B2 | 8/2003 | Quy | |
| 2002/0016719 A1 | 2/2002 | Nemeth et al. | |
| 2002/0019584 A1 | 2/2002 | Schultze et al. | |
| 2002/0026223 A1 | 2/2002 | Riff et al. | |
| 2002/0072785 A1 | 6/2002 | Nelson et al. | |
| 2002/0082480 A1 | 6/2002 | Riff et al. | |
| 2002/0120310 A1 | 8/2002 | Linden et al. | |
| 2003/0004554 A1 | 1/2003 | Riff et al. | |
| 2003/0072424 A1 | 4/2003 | Evans et al. | |
| 2003/0139785 A1 | 7/2003 | Riff et al. | |
| 2003/0204413 A1 | 10/2003 | Riff | |

OTHER PUBLICATIONS

Jack Smith ; Your Personal Health Buddy; ABCNews.com; http:/abcnews.go.com/sections/tech/CuttingEdge/cuttingedge990225.html; 3 pages (Nov. 24, 2000).

The Health Hero Communications Platform ; The Health Hero Network Online Services ; http:/www.hhn.com/products/index.html ; 2 pages (Nov. 24, 2000).

Painless Blood–Glucose Monitoring ; Kumertrix Technology Overview ; http:/www.kumertrix.com/technology.html; 2 pages; Nov. 24, 2000.

Technology & Clinical Results–Simple Solutions Through Technology–Progression of Glucose Monitoring Technology ; Amira ; http:/amira.com/tech/tc_tech.htm; 2 pages; Nov. 24, 2000.

Wired for Wellness ; LifeChart.com ; http:/www.lifechart.com ; 2 pages ; Nov. 24, 2000.

About Data Critical Corporation ; Yahoo—Data Critical to Provide Mallincrodt with Wireless Connectivity for Ventilators ; http:/biz.yahoo.com/prnews/001012/mo_mallinc.html; 1 page; Nov. 24, 2000.

Bluetooth wireless technology–bridging the gap between computing and communication; Bluetooth Technology; http://www.intell.commobile/bluetooth/; 2 pages; Nov. 28, 2000.

Bluetooth resource center ; What is Bluetooth ?; palowireless.com; http:/www.palowireless.com/infotooth/watis.asp; 3 pages; Nov. 28, 2000.

Bluetooth Tutorial ; palowireless.com—bluetooth resource center ; http://www.palowireless.com/infortooth/tutorial.asp; 4 pages; Nov. 28, 2000.

Bluetooth Profiles; palowireless.com—bluetooth resource center; http://www.palowireless.com/infortooth/tutorial/profiles/asp; 4 pages; Nov. 28, 2000.

Nick Hunt ; Bluetooth Venus 802.11 ; TDK Systems ; http://www.cellular.com.za/bluetooth_802.htm; 4 pages; Nov. 28, 2000.

Bluetooth vs. Airport (802.11 Network); palowireless.com—Bluetooth resource center; http://www.palowireless.com/infotooth/knowbase/othernetworks/15.asp; 3 pages; Nov. 28, 2000.

Personal Digital Assistants; A2 Anytime/Anywhere—A Weekly on Wireless Infrastructure and Data Services; Thomas Weisel Partners (Merchant Banking); 5 pages; Nov. 29, 2000.

Ashlee Vance; Ericsson and Intel Make Bluetooth Pact; Infoworld.com; http://www.infoworld.com/articles/hn/xml/00/12/04/001204hnericintel.xml?T.../printarticle.htm; 1 page; Dec. 4, 2000.

Personal Portable Office; Nokia 9000il digital; http://www.nokiausa.com/9000il; 4 pages; Dec. 7, 2000.

Pui–Wing Tam; Handspring Homes; Article from the Wall Street Journal; Section B; Nov. 2000.

Author unknown; Articles on Phones and New Technologies; Article from the Wall Street Journal; Nov. 2000.

David Pringle; Sagen to Launch Hand–held Computer that Doubles as Top–End Mobile Phone; Article from the Wall Street Journal; Nov. 2000.

Svensson, Peter; "Cisco Launches WiFi Phone" Article from Australian IT; Apr. 29, 2003.

"Breakthrough Devices Shown At ADA" published in Diabetes News for Jul. 1, 2001 at http://www.diabetesnet.com/news/news070101.php.

"iMetrikus" published at http://www.qualcomm.com/qwbs/resource/resourcelib casestdy.shtml.

"Applications of MedStar" published on Apr. 27, 2003 by Cybernet Medical, 16 pages.

"HIPAA & WiFi: Regulatory Tangles for Wireless Health Care Networks Analyzed" published at http://www.hipaadvisory.com/tech/wireless.htm.

"Medtronic CareLink Network, How It Works" published at http://www.medtronic.com/carelink/features.html.

"FDA Approves Medtronic Carelink™ Monitor and Software, Opening a New Chapter in Patient Management Using Internet Technology", Medtronic News Release dated Jan. 2, 2002.

"The MedStar System, How the MedStar System Works" brochure published by Cybernet Medical.

"iMetrikus Mobile Solutions" brochure by iMetrikus, Inc.

"Instromedix—Products" published at www.instromedix.com/pages/products/products.asp. 7 Pages.

* cited by examiner

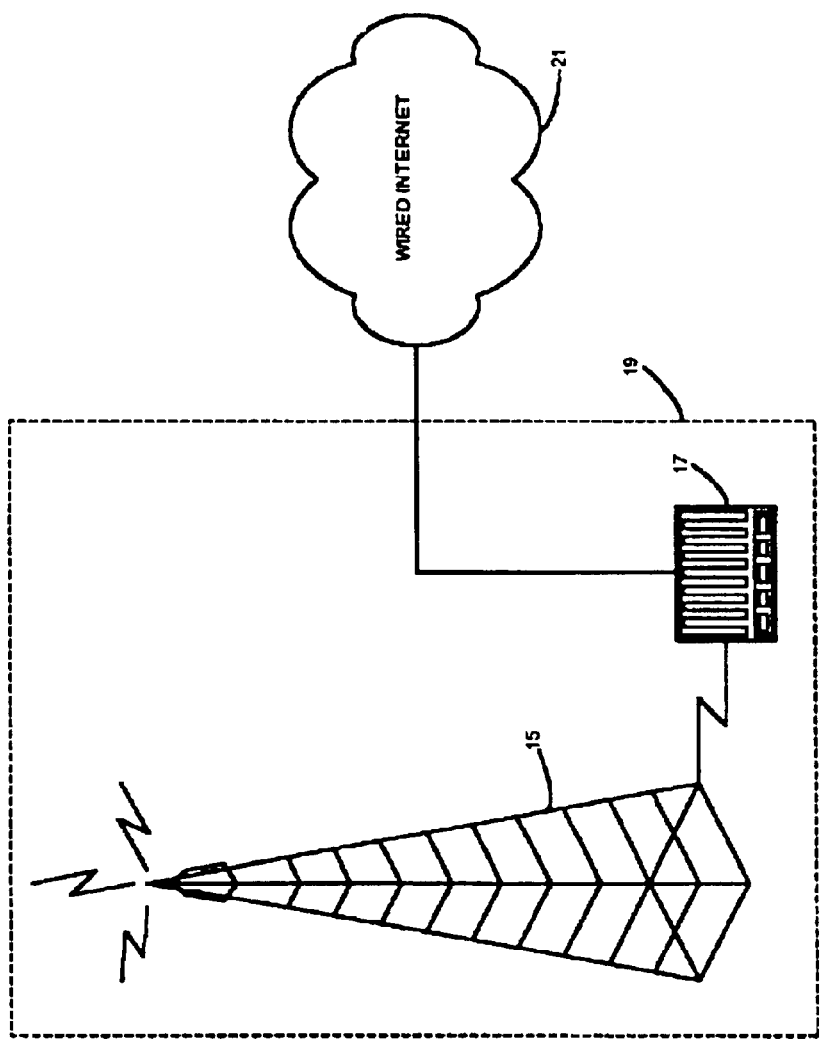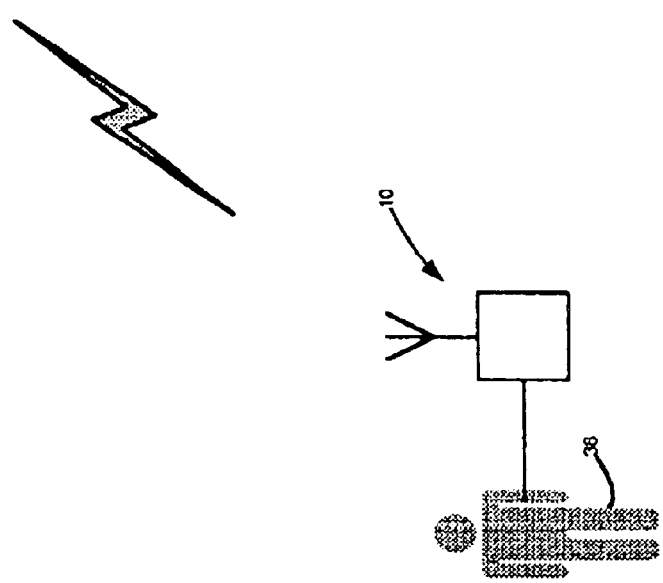
FIG. 1

METHOD AND APPARATUS FOR HEALTH AND DISEASE MANAGEMENT COMBINING PATIENT DATA MONITORING WITH WIRELESS INTERNET CONNECTIVITY

CROSS-REFERENCE TO RELATED APPLICATIONS

This application is a continuation-in-part of U.S. patent application Ser. No. 10/418,845, filed Apr. 18, 2003, which is a continuation of U.S. patent application Ser. No. 09/738,270, filed Dec. 15, 2000, now U.S. Pat. No. 6,602,191.

REFERENCE TO GOVERNMENTAL SUPPORT (none)

REFERENCE TO MICROFICHE APPENDIX (none)

FIELD OF THE INVENTION

The present invention relates to monitoring of living subjects, and more particularly to health-monitoring of persons where measured or input health data is communicated by a wireless device to and from a software application running on an internet-connected server and where the same may be studied and processed by the software application, a health professional, or the subject.

BACKGROUND OF THE INVENTION

Several attempts have been made in the past to achieve efficient interactive communication of medical or health information between a subject or patient and a reviewer or provider of that information. In particular, communication of consumer physiological information has been a subject of such attempts. It is noted that in this regard the "reviewer or provider of medical or health information" is understood to include not only a physician but also a software application or algorithm that may analyze the information.

Medical or health information has been made available on a CD-ROM accessible by a home computer system. This passive approach had certain disadvantages. First, although the personal computer is prevalent is the United States, it is generally too expensive for a consumer physiological monitoring system and there are many people who find it too complicated to set up and use for that purpose. High-risk, chronically ill patients, responsible for more than half of health care costs in the United States and forming the fastest growing segment of those requiring health care, are indeed the most likely not to be able to afford or use a system built around a personal computer. In addition, such systems are limited in their interactivity to the information stored on the CD.

Previous patents by the Inventor addressed both of these disadvantages, as well as the need to reduce health care costs through providing educational health care information and interactive physiological monitoring in the home environment by means of a user-friendly, interactive system (see, e.g., U.S. Pat. Nos. 5,601,435, 6,144,837, and continuations thereof).

These previous patents were based on a video game console, or a multimedia player using a conventional television screen as the display device to achieve a system which is simpler to use than systems based on a personal computer. An initial embodiment of the previous patents utilized a compact disc to provide interactive information for disease management.

Even with the advantages provided, these systems limited the user to location in which the device was located. Even where devices are portable, as in the case of a laptop computer with a modem, an ordinary POTS phone line must be found and used. Where the user's computer employs a broadband connection, such as DSL or satellite, the choices of location are even more limited.

Attempts have been made to remedy this deficiency. For example, many telemetry systems allow a "wireless" distance to be placed between a health measuring unit and a remote monitoring system. However, such systems are limited in their range.

Other systems have used cellular telephone technology to increase the wireless health monitoring range. However, these systems have several deficiencies, such as requiring significant modification of the mobile phone. For example, U.S. Pat. No. 5,772,586, issued Jun. 30, 1998 to Heinonon et al., discloses a method for monitoring the health of a patient. This system uses a specialized connection between the patient health measuring unit and the cellular phone, however. The patient health measuring unit is located in the battery space of the mobile phone and is connected to a communication bus of the mobile phone. Other systems have been proposed, but these suffer from similar deficiencies in that they are not designed to be used with "off-the-shelf" wireless devices or health measuring equipment.

The deployment of the above systems also currently lacks employment of full back-end server functionality with which to provide a wide range of interactive communication with the patient. Instead, such systems, if internet-enabled, are often limited to mere one-way non-interactive data transfer via a modem. While some systems are more enhanced, including that disclosed in U.S. Pat. No. 5,357,427, issued Oct. 18, 1994 to Langen, et al., and entitled "Remote Monitoring of High-Risk Patients using Artificial Intelligence", these systems are limited by the wired telecommunications infrastructure.

SUMMARY OF THE INVENTION

Embodiments of the present invention overcome one or more of the disadvantages of the prior art by providing a full-feature health-monitoring system that may wirelessly connect to a back-end server application via the internet. The invention allows wireless access to and from a wide variety of present medical or health-related instruments and devices, while maintaining the capability of connecting to future such devices.

In particular, the invention may be embodied in several systems. Two complementary such systems are described herein, although extensions to other such systems can be envisioned. First, an embodiment of the invention may be employed to manage the disease state or condition of a patient. In this embodiment, the patient may employ a health monitoring device ("HMD"), in particular a medical device, and a wireless connection to provided data from the medical device for processing via the internet including a review by a physician or other health care professional if required.

In the second embodiment, a health or lifestyle management plan may be implemented. Various health parameters, such as those relating to nutrition or exercise, may be entered into a health monitoring device, in this instance termed an "exercise machine", and the same may be wireless communicated to a server. An application may process and store the health parameters, and a health specialist may optionally review the same.

Wireless internet connectivity has many advantages. For example, in the first embodiment, a diabetic could connect a blood glucose meter to an internet-enabled wireless web device ("WWD") away from home and download data to a Diabetes Management Company's server and, in response, receive guidance displayed on the screen (or by voice) about choices for the next meal.

Alternatively, in the second embodiment, a person interested in tracking an exercise program may take the WWD to the local health club and attach the same to an exercise machine, send data output from various exercise machines over the Internet, and receive a personalized response from the server of a company specializing in Health & Lifestyle Management. The individual may input caloric content of foods eaten, and may further input caloric content of exercise performed. In this way, e.g., a person in a weight-loss program may see in great detail whether they are expending more calories in the form of exercise than the same individual is consuming in the form of food.

In general, in the health management embodiment, the system may be employed to monitor the physiologic status of a healthy subject while eating, exercising, or performing other activities. For clarity, such devices are termed herein "exercise machines". These may include an electronic body weight scale, a body fat gauge, biofeedback devices, physiotherapy or chiropractic equipment, blood pressure recorders, or the like, or any type of exercise machine or monitor, including a heart rate monitor, treadmill, rowing machine, stepper, or the like.

In more detail, the present invention provides a method and system for assisting patients to manage a disease or maintain healthy lifestyle by collecting health-related data and providing information in response to those data by means of a WWD designed to display interactive information through a connection to the Internet. The present invention may be connected to various HMDs, both medical and exercise-related in nature, and may communicate information via a wireless connection such as a wireless Internet connection.

A major advantage of embodiments of the invention is that the same frees the patient from the constraints of wired systems. The same allows users with consumer "off-the-shelf" wireless devices to significantly extend the range of connectivity over that of wired computer, television, or even wireless telemetry systems.

In a first embodiment of the present invention, the WWD is a web-enabled mobile phone. Here it is noted that the term "web" or "internet" are used interchangeably to refer to the internet in general. In a second embodiment, the WWD is a palm, handheld, or laptop computer, or a PDA, equipped with a wireless modem. In a third embodiment, the WWD may be a hybrid device that combines the functions of a computer, PDA and telephone.

An adaptor is used if necessary to convert the output signal of the medical monitoring device to a suitable input signal for the, e.g., WWD. The adaptor allows connection of the WWD to a medical device, exercise machine or other variety of health care equipment, and the connection may be made via several techniques. As for wired techniques, a standard USB, USB2, Firewire, parallel bus or serial cable may be used if the input/output ports between the HMD and the WWD are appropriate. Otherwise, a suitable separate adaptor may be employed.

The connection may also be an input such as a disk drive or other media input for input of data, a USB port or phone jack or other such wired input, again employing an adaptor if required.

As for wireless techniques, infrared (IR), microwaves, radio frequency (RF), e.g., Bluetooth® or 802.11 protocols, optical techniques including lasers, and other such techniques may be used. The patient or subject may also input data manually, such as by a stylus, keypad, synchronization from a PC, or by various other techniques discussed below.

A major advantage of the invention is that by use of an optional adaptor, the system is compatible with current and prior HMDs as well as maintaining a capability of adapting to future such systems.

Other advantages of the invention may include one or more of the following. An embodiment of the invention may be used when a patient is traveling or otherwise away from their "wired" means of communication. The invention allows wireless health-monitoring to the level of accuracy previously achieved only by desktop so-called "wired" computer systems. The invention is protocol-independent.

The interaction between a WWD and a back-end server may provide a major additional advantage in certain embodiments of the invention. In particular, the relatively small amount of memory currently provided on a WWD as compared to a back-end server severely limits the functionality of applications running on the WWD, especially in terms of computing capacity, processing power, and user interface. By providing significant application functionality on the back-end, less memory and processing capabilities become necessary on the WWD (i.e., on the "front-end"). Thus, memory may be used in the WWD for an enhanced user interface or for other purposes, according to the user requirements.

In a method according to an embodiment of the invention, the patient connects to a specific Internet site and a software program, resident on a remote server located on the Internet, downloads an interactive user interface for that patient and an application for the measurement of the physiological data. The software may also be downloaded to the WWD from a personal computer via a synchronization operation in known fashion. The software provides a personalized display for the user and configures the WWD to control and monitor devices connected via a generic input/output port to the WWD. The software may be designed to suit the constraints of the small display screens of WWDs. The software, as well as inputs from the patient or other inputs, can control the manner, content, and display of information presented to the patient, and measured or input data can be stored for review by a health care provider or by a software algorithm or application. The algorithm may be of varying complexity, from a simple program that merely acknowledges receipt of information to an artificial intelligence algorithm, such as an expert system, collaborative filtering system, rules based system, case-based reasoning system, or other such artificial intelligence application.

Further information may be provided to or from the patient, including information entered manually. The patient may input this information via a personal computer, which then may download the input information to the WWD via a synchronization operation using standard protocols, such as those for Palm PDA devices.

The user may also input supplemental information via a PC connected independent to the server via the internet. Such supplemental information may include data that is difficult or inconvenient to input on the WWD. In this way, the patient may be afforded a more convenient environment in which to manipulate data to supplement the data input to the WWD. The deployment of voice processing technology may be used to enable an even more convenient user interface: i.e., one to which patients can talk.

In all of these respects, the portable aspect of the WWD is important: to wit, the user may conveniently carry the WWD on their person wherever they may go, allowing data entry at the time needed.

Other aspects, features, and advantages will be apparent from the summary above, as well as from the description that follows, including the figures and the claims.

BRIEF DESCRIPTION OF THE DRAWINGS

FIG. 1 illustrates a general embodiment of a wireless health-monitoring system according to the present invention;

DETAILED DESCRIPTION OF THE PREFERRED EMBODIMENTS

Figure 2:
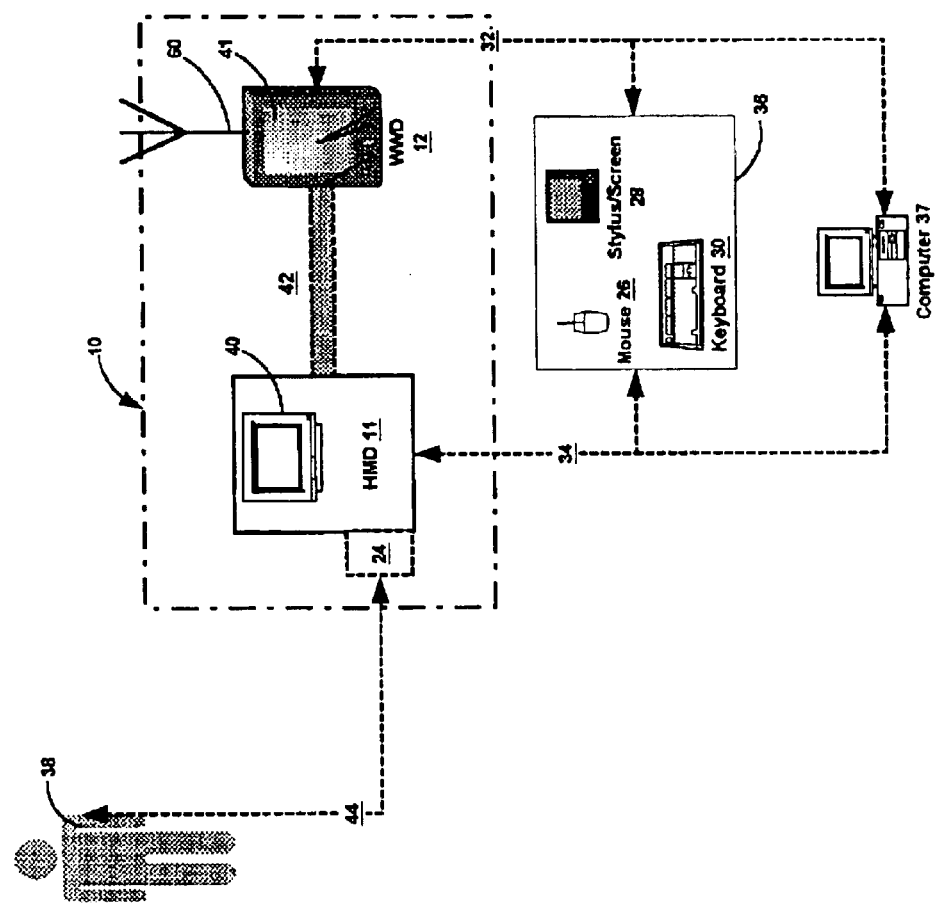
FIG. 2 illustrates an embodiment of a wireless health-monitoring apparatus according to the present invention, showing the system of FIG. 1 up to a point of a wireless antenna.

Various acronyms are used for clarity herein. Definitions are given below.

The term "HMD" may encompass not only devices with physiologic sensors but also devices with a keypad, keyboard, mouse, pointer, pressure sensor, or other such inputs that the patient or user may employ to perform data entry of the desired parameters. In general, HMDs include some means for determining a health parameter.

In a disease management embodiment, an HMD may be a blood glucose monitor, a blood pressure monitor, an ambulatory ECG recorder, a respiratory monitor, a temperature or heart rate monitor, and so on.

In a healthy lifestyle management embodiment, an HMD may be an exercise machine, including treadmills, rowers, steppers, exercise cycles, or other aerobic or anaerobic exercisers, or a monitor, include monitors for temperature, heart rate, blood pressure, amount of work or rate of work performed, etc.

The term "subject" as used herein primarily indicates a human subject. The same may be a medical patient under physician care, a person interested in maintaining health via accurate recording of nutrition and exercise, and so on. The term "user" is generally used to refer to the user of the device, which may be synonymous with the subject or may alternatively be a caregiver of the subject, etc. The term "patient" is used, in addition to a person under the care of a physician, to also refer to a "normal" or healthy individual who is interested in maintaining a healthy physiologic balance.

The term "signal communication" is used to mean any type of connection between components where the connection is, e.g., electromagnetic, and where the connection allows information to be passed from one component to another. This term may be used in a similar fashion as "coupled", "connected", "information communication", "data communication", etc. The following are examples of signal communication schemes. As for wired techniques, a standard bus or serial cable may be used if the input/output ports are compatible and an optional adaptor may be employed if they are not. As for wireless techniques, IR, microwaves, RF, e.g., Bluetooth® or 802.11 protocols, optical techniques including lasers, and other such techniques may be used. The patient or subject may even input data manually, such as by a stylus or keypad or by various other techniques discussed above and below.

The term "generic input/output port" is used to mean any type of convention, standard, universal, stock, consumer, or "off-the-shelf" type of port for data input and output. These may include both wired and wireless ports. A further description is given below.

Various embodiments of the invention are now described in more detail.

Referring to FIG. 1, a system of the present invention is shown for monitoring health data from a patient or subject 38. The system includes a wireless health-monitoring apparatus ("WHMA") 10 described in further detail below. WHMA 10 is linked in a wireless fashion to a wireless connection point of presence ("POP") 19, the same including at least a base station antenna 15 coupled to a server 17. Server 17 is in turn connected to the wired, or even a wireless (not shown) Internet 21, which may include the World Wide Web.

Referring to FIG. 2, an first embodiment of WHMA 10 is shown. WHMA 10 includes an HMD 11, which may include an optional monitor screen 40, coupled via an optional adaptor 42 to a WWD 12. WWD 12 connects wirelessly via an antenna 60 to base station 15 (see FIG. 1). One function of WWD 12 is to provide the user interface; other functions are described below.

As noted above, HMD 11 may include a physiologic sensor 24 or may include a manual system 36 for input of physiologic data via a connection 34. Manual system 36 may also be used to input data directly into WWD 12 via a connection 32. Manual system 36 may include, e.g., a keyboard 30, a mouse 26, a pen-type device 28, and may also employ a separate monitor (not shown). Of course, the user may also view information on monitor 40 or on a screen 41 of WWD 12. In many embodiments, the stylus-based system employed by many current PDA's, such as the Palm®, may be preferred for such manual data input.

Data may also be input via entry on a computer 37. This data may then be synchronized to WWD 12 in known fashion. Alternatively, computer 37, or another computer (see computer 37' in FIG. 4) may be used to connect to a server using the wired internet. This use may be particularly advantageous when entering a large amount of data, such as a patient's medical history. As noted above, in this way the patient may be afforded a more convenient environment in which to manipulate data to supplement the data input to the WWD.

It will be clear to one of skill in the art given this teaching that cable 32, as well as cables 34 and 44, may be replaced with wireless circuitry to communicate signals wirelessly. Alternatively, cables 34 or 44 may be replaced by a direct plug and socket connection.

For medical devices and applications, physiologic sensor 24 may include, e.g., a sensor appropriate for measuring blood glucose levels, blood pressure, heart rate, or any other desired parameter as required by the physician. Sensor 24 may connect via an optional cable 44 to subject 38. Alternatively, sensor 24 may be distal of HMD 11, i.e., at or within subject 38. In other words, if cable 44 is employed, sensor 24 may be proximal or distal of cable 44. If a wireless communications capability is added, sensor 24 need not physically connect with HMD 11 or WWD 12 at all. That is, the same may measure a health parameter and may communicate the same to wireless health-monitoring apparatus 10 wirelessly. The short range wireless communications schemes which may be employed include infrared, radio frequency including Bluetooth or 802.11, or other such schemes.

As examples of sensor types, to measure blood glucose levels, sensor 24 may be a sensor that accepts a drop of blood, e.g., via a finger-prick. To measure heart rate, sensor 24 may be placed via an adhesive sensor disposed on the chest. Other health monitors may also be employed so long as the measured data may either be transferred to WWD 12, e.g., via optional adaptor 42, described in further detail below, or by being read by a user, e.g., from a display, and manually input to WWD 12. Alternatively, the measured data may be transferred to WWD 12 via wireless communication schemes, such as RF includes Bluetooth® or 802.11, infrared, optical, microwaves, etc., directly from sensor 24 or from HMD 11 as described in greater detail below. The measured data may be obtained by an implantable device, such as a cardiac monitor, for which a wireless communication scheme would be particularly appropriate.

The user, who may or may not be the same person as subject 38, may input data to WWD 12 from history or experience. For example, in a health or exercise device, if subject 38 consumes a known number of calories, this information may be entered via manual system 36 directly into WWD 12 or into HMD 11. Further, the user, the subject, and the sensor are not necessarily the sole sources of information. Data stored on the server, or on a separate server operated for health management may also be employed to result in a health benefit to subject 38.

Figure 3:
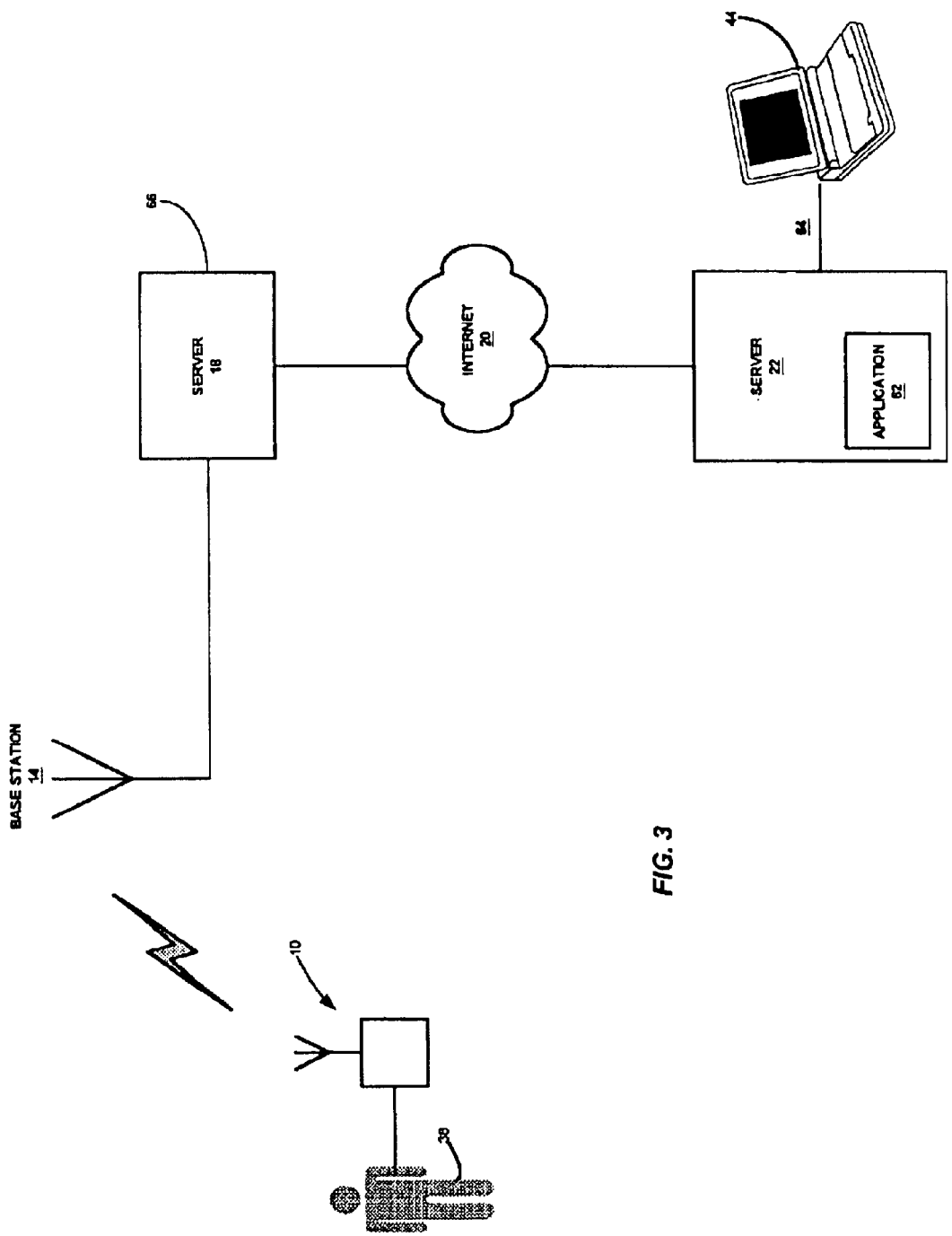
FIG. 3 illustrates an embodiment of a back end of a health-monitoring system according to the present invention.

Referring to FIG. 3, WHMA 10 is shown communicating wirelessly with the Internet. In doing so, WHMA 10 generally sends a wireless signal to a base station 14 (in known fashion) that is connected to a server 18 that is in signal communication (in known fashion) with the internet. Server 18 communicates via a protocol (in known fashion) to Internet 20, which also communicates via a protocol (in known fashion) to a server 22 running an application 62. Server 22 may be accessed (in known fashion) by a client computer 44 through a connection 64.

As noted, the protocols for data communication are known. However, they currently vary amongst known techniques. The present invention is not limited to any particular protocols, and may be implemented in any languages supported by the WWD and server. Of course, as computing capabilities continue to increase, it is expected that the capabilities of WHMA 10, servers 18 and 22, as well as application 62 and client 44, and other components, will correspondingly increase.

Figure 4:
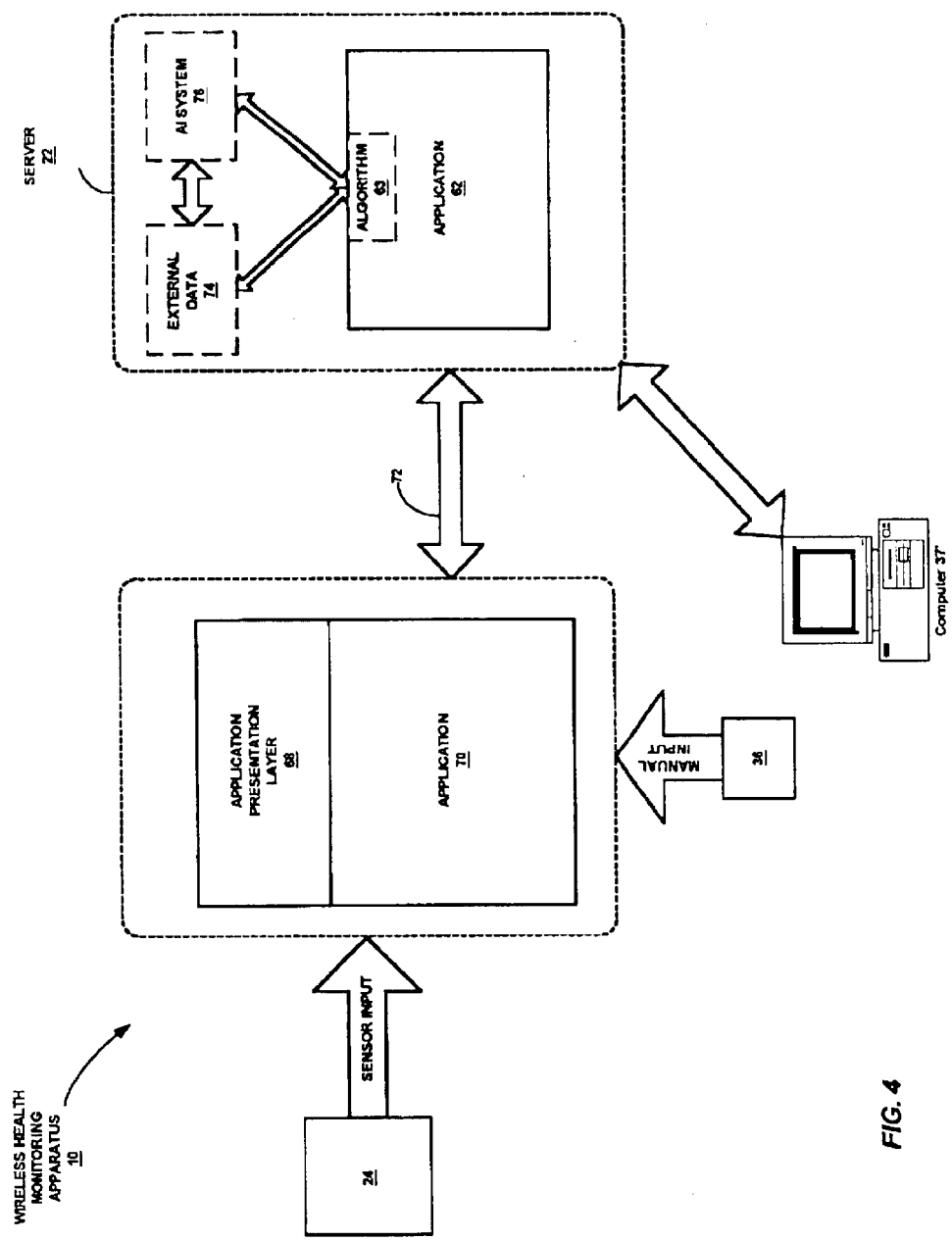
FIG. 4 illustrates a data flow diagram according to an embodiment of the present invention.

Application 62 running on server 22 may interact with WHMA 10 in a number of ways. Referring to FIG. 4, WHMA 10 is shown in signal communication with server 22 via a connection 72. Connection 72 schematically represents the wireless Internet connection and intervening pathways. WHMA 10 includes an application that may be viewed as having two components: a base wireless or device application 70 and an application presentation layer or user interface 68. User interface 68 is employed to, e.g., present a menu of options to the user, to allow the user to choose inputs, and to generally operate the device. User interface 68 may vary widely in sophistication, e.g., from a simple data entry field to a full graphical user interface. These applications may accept as inputs data from a sensor 24 as well as from a manual input 36.

Server 22 has a base server application 62 with which the same calculates or provides a response based at least in part on data from WHMA 10. Application 62 may include an algorithm 63 for analyzing data from the HMD, and either application 62 or algorithm 63 may optionally access data from an external data source 74 and may further consult an artificial intelligence system 76.

External data source 74 may be a memory or disk or other such storage that stores health data, such as healthy and unhealthy weight/height ranges, healthy and unhealthy cholesterol counts, the patient's or subject's prior medical or health history, healthy and unhealthy blood pressure values, information corresponding to the caloric and other nutritional content of foods, information corresponding to the caloric expenditure values of various exercises, algorithms for calculating various health parameters, etc. In general, any data that may benefit the health of a subject or patient may be stored in external data source 74. External data source 74 may also include online access of health information from external web sites, ftp servers, or other sources.

Due to the current relatively small amount of memory and storage available on current WWDs, such external application processing as by application 62 and external data storage as by external data 74 may be particularly important.

As noted, application 62 or algorithm 63 may also consult AI system 76 for suggestions as to health benefits. AI system 76 may even interact with external data source 74 to extract useful information from the same. AI system 76 may employ, e.g., case-based reasoning, rules-based systems, collaborative filtering, neural networks, expert systems, or other such systems as are known.

It should also be noted that each of application 62, algorithm 63, external data source 74, or AI system 76, may physically reside on more than one server, e.g., on an array of servers for, e.g., storage or multiple processing purposes. Each of application 62, algorithm 63, external data source 74, or AI system 76, or combinations of each, may also respectively reside on different servers.

The extent to which server application 62 interacts with wireless application 70 depends on the use to which the system is put. For example, in a less interactive embodiment, device application 70 may act to measure a diabetic patient's blood glucose level and report the same to server application 62. In this case, a physician may simply review the measured value and send the patient an email reporting that the value is acceptable or not. In a highly interactive embodiment, a patient may have numerous HMDs 11 connected via optional adaptors to a WWD 12, and wireless application 70 may correspondingly send a large amount of health data to server application 62. The physician, accessing server application 62, may in turn send detailed care plans to a caregiver via connection 72. The received data may be analyzed using algorithm 63, external data source 74, and AI system 76. In this sense, the two applications may be highly interactive.

It is noted that an Application Service Provider (ASP) may operate application 62. That is, application 62 may be leased by an ASP to the health care provider, and the ASP may perform all necessary upgrades and maintenance to application 62 and its associated components.

To initialize the system, the program starts and a wireless application is loaded into the WWD. The loading of the wireless application may occur via synchronization from a desktop or via downloading from a server over the internet. The server application may be loaded into an appropriate internet-connected server. Subject data may be loaded into the WWD or into the server. In the latter case, the subject information may later be transferred to the WWD or transferred to the server from the WWD, as called for by the application. The initialization scheme then ends.

The wireless application may access the server and server application, or vice-versa, as determined by the respective program instructions. Examples are now given for (1) a system of disease and patient management and (2) a system for health management employing an exercise machine.

Example Employing System For Disease Management

Figure 5:
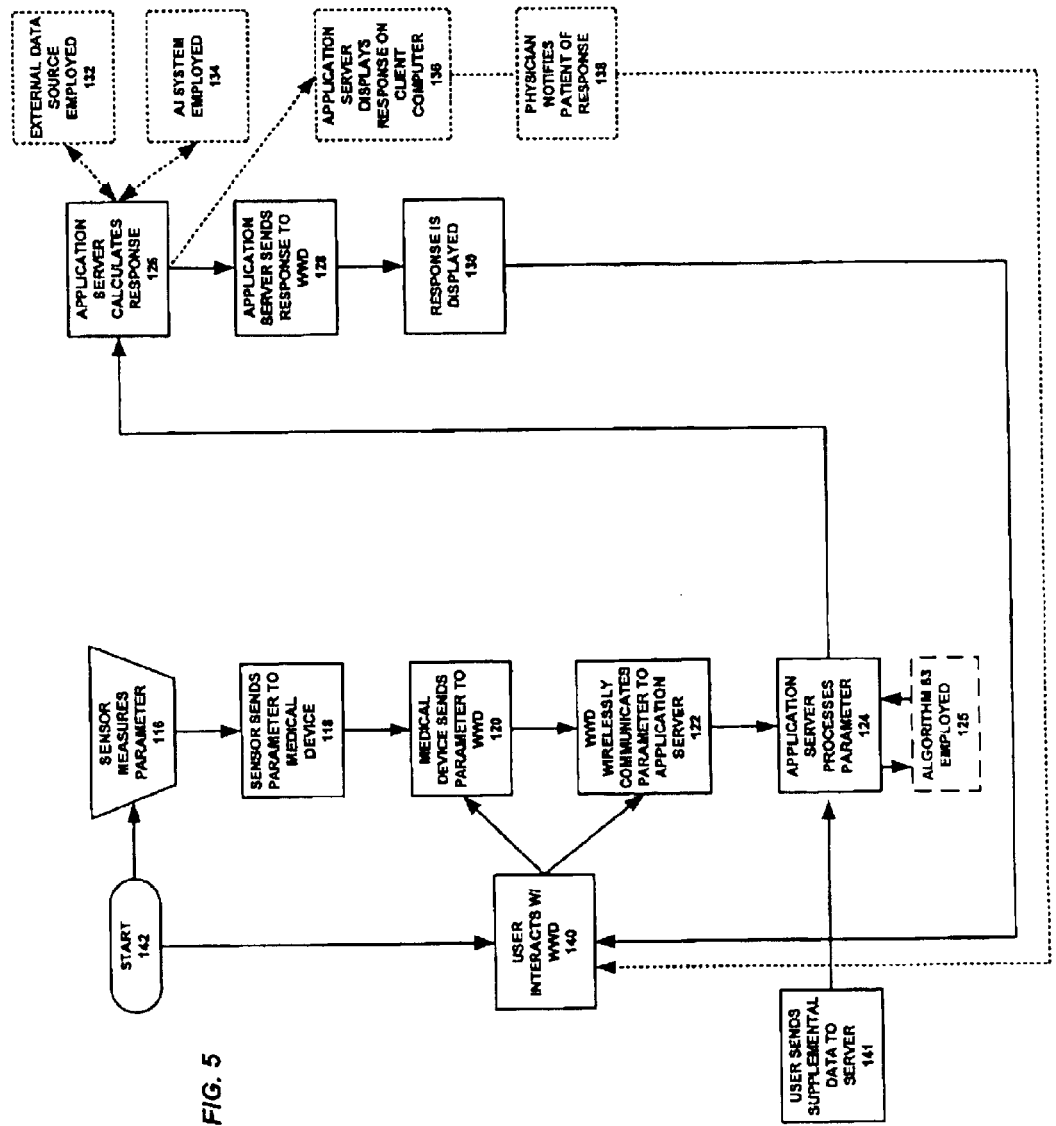
FIG. 5 illustrates an embodiment of a method of use for a wireless application and a server application according to the present invention, in which the same is implemented for disease and patient management.

Referring to FIG. 5, an example is given for a system of disease and patient management. In this figure, as well as in FIG. 6, boxes in dotted lines may generally be considered optional.

In FIG. 5, a medical device may determine health parameters and an optional physician review is provided. Health parameters may also be determined by user manual input.

The program is started (step 142) and a sensor measures a health parameter (step 116). The sensor may send the parameter to a medical device (step 118). The medical device then sends the parameter to the WWD (step 120). The WWD then wirelessly communicates the parameter to the application server (step 122), e.g., via the wireless web. The application server processes the parameter (step 124), and calculates or provides a response (step 126) based at least in part on the parameter. The application server may optionally employ algorithm 63 (step 125), external data (step 132) or an AI system (step 134) in the calculation. The application server then sends the response to the WWD (step 128), where the response is displayed (step 130).

It should be noted that the term "response" here is used generally may simply be an acknowledgement that the parameter was received by the application server. The term "calculate" is also used generally, and may entail a simple calculation as well as a complex one. A result may, e.g., be the result of a calculation.

As noted above, the sensor may connect to any type of medical device or other such device in which information pertaining to a patient's disease or condition may be ascertained. The parameter may be any value corresponding to such information.

The method may also use a manual input as shown. In this case, after the start (step 142) of the application, the user may interact with the WWD (step 140). The interact may be a data input, a command to read data from a medical device, a response to a physician question or statement, an acknowledgement of physician notification, etc. Calculations by the application server may further take into account supplemental data sent by the user to the server, e.g., in a wired fashion directly over the internet (step 141).

FIG. 5 also shows a physician review and notification. In this option, the responses are displayed on a client computer (step 136) in signal communication with the application server. A physician may then review the response on the client computer, and notify the patient of the responses (step 138). For example, the physician may notify the patient of positive or negative responses. Of course, it should be noted that the "client computer" may simply be a pager, PDA, WWD, or other such device, as well as a more typical desktop or laptop computer.

In one implementation, a diabetic may keep a database on a server of a dietary history and a blood glucose history. With this data at-hand wirelessly, the diabetic may choose whether to eat a particular food by entering nutritional information about the food into a WWD, transmitting the same wirelessly to the server, and receiving a recommendation from the server. The recommendation may be based on the food and also on data or information that had previously been transmitted wirelessly, including data from a blood glucose monitor, data input manually, if any, as well as data from algorithm 63, external data source 74, and AI system 76.

Example Employing System for Health Management Using a General Exercise Machine

Figure 6:
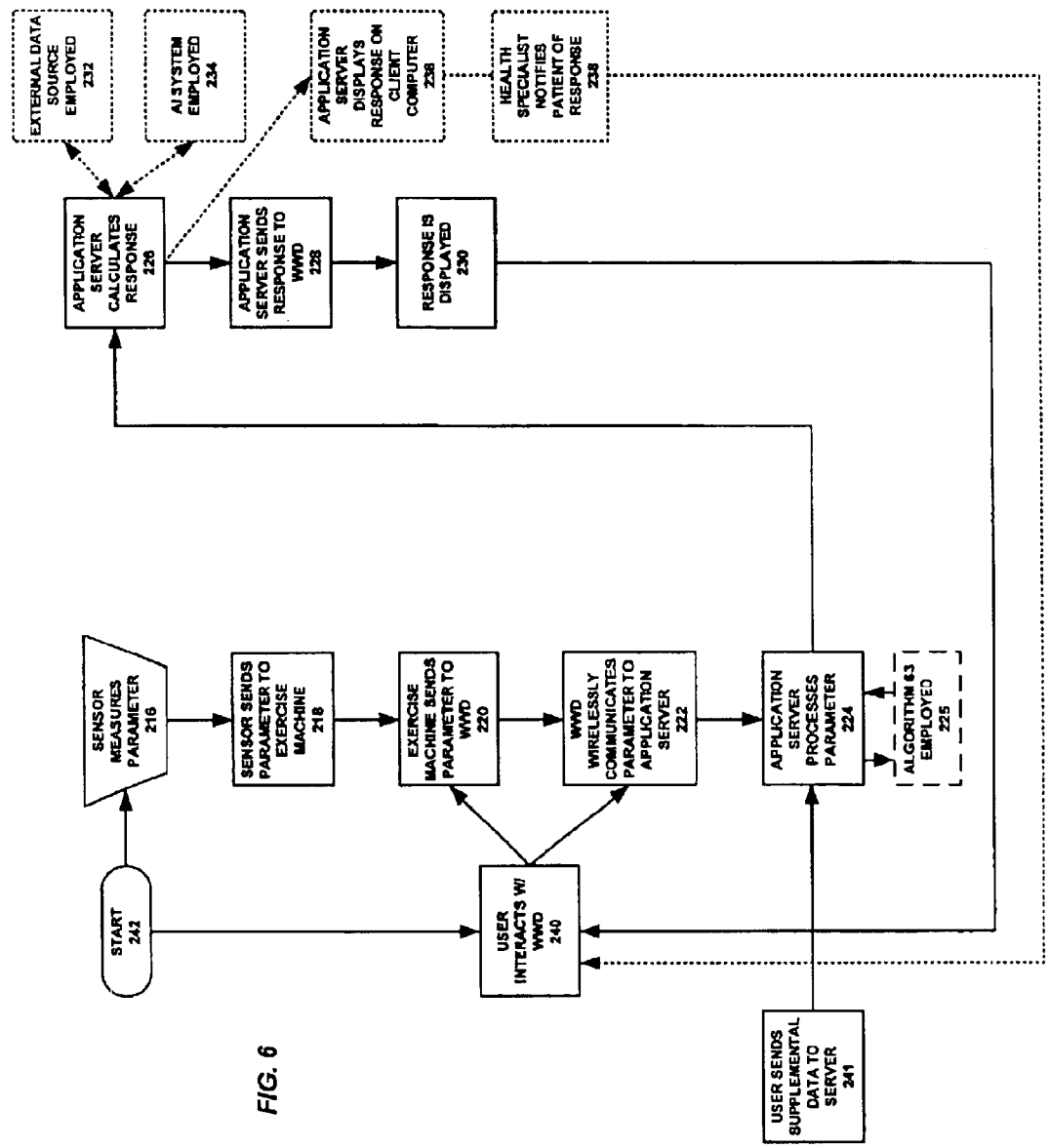
FIG. 6 illustrates an embodiment of a method of use for a wireless application and a server application according to the present invention, in which the same is implemented for health management.

Referring to FIG. 6, an example is given for a system of health, nutrition, and/or exercise management. In this example, the HMD is an exercise machine as that termed has been defined above.

The program is started (step 242) and a sensor measures a health parameter (step 216), where the health parameter corresponds to health, fitness, nutrition, exercise, etc. The sensor may send the parameter to the exercise machine (step 218). It is understood here that the "sensor" may be, e.g., a blood pressure monitor, but may also be a simple device connected to an aerobic exerciser that tracks miles ran, work performed, etc.

The exercise machine then sends the parameter to the WWD (step 220). The WWD wirelessly communicates the parameter to the application server (step 222), e.g., via the wireless web.

An alternative and complementary way of entering the parameter is by user input (step 248). For example, the user may enter the parameter into the exercise machine or into the WWD. This parameter may correspond to an amount of exercise performed, an amount of food consumed, etc.

Calculations by the application server may also take into account supplemental data sent by the user to the server, e.g., in a wired fashion directly over the internet (step 241).

The application server processes the parameter (step 224 and optionally step 225), and calculates a response (step 226) based at least in part on the parameter. The application server may optionally employ external data (step 232) or an AI system (step 234) in the calculation. The application server then sends the response to the WWD (step 228), where the response is displayed.

The same definitional statements regarding the terms "response", "calculate", "sensor", etc., as given before, apply in this embodiment as well.

As an optional step, a health specialist may notify the patient or subject of the response (step 238) after having the same displayed on their client computer (step 236). The health specialist may be replaced in this example by an application that may also include an algorithm.

Adaptor Hardware

A description is given below of a particular type of adaptor hardware. As noted above, the adaptor may optionally be used to connect a HMD to a WWD.

In general, a connection is necessary between a HMD 11 and a WWD. The nature of this connection may vary. For example, the connection may be wired or wireless. For wired systems, the connection may be direct or an adaptor may be employed, either on one or both ends of the direct wired connection, to adapt the signal appropriately. In the same way, for wireless systems, the connection may be direct, if both HMD and WWD employ the same wireless protocol, or an adaptor may be involved to modify the signal of one or both devices. These connections, all of which are encompassed by the present invention, are discussed in more detail below.

Figure 7:
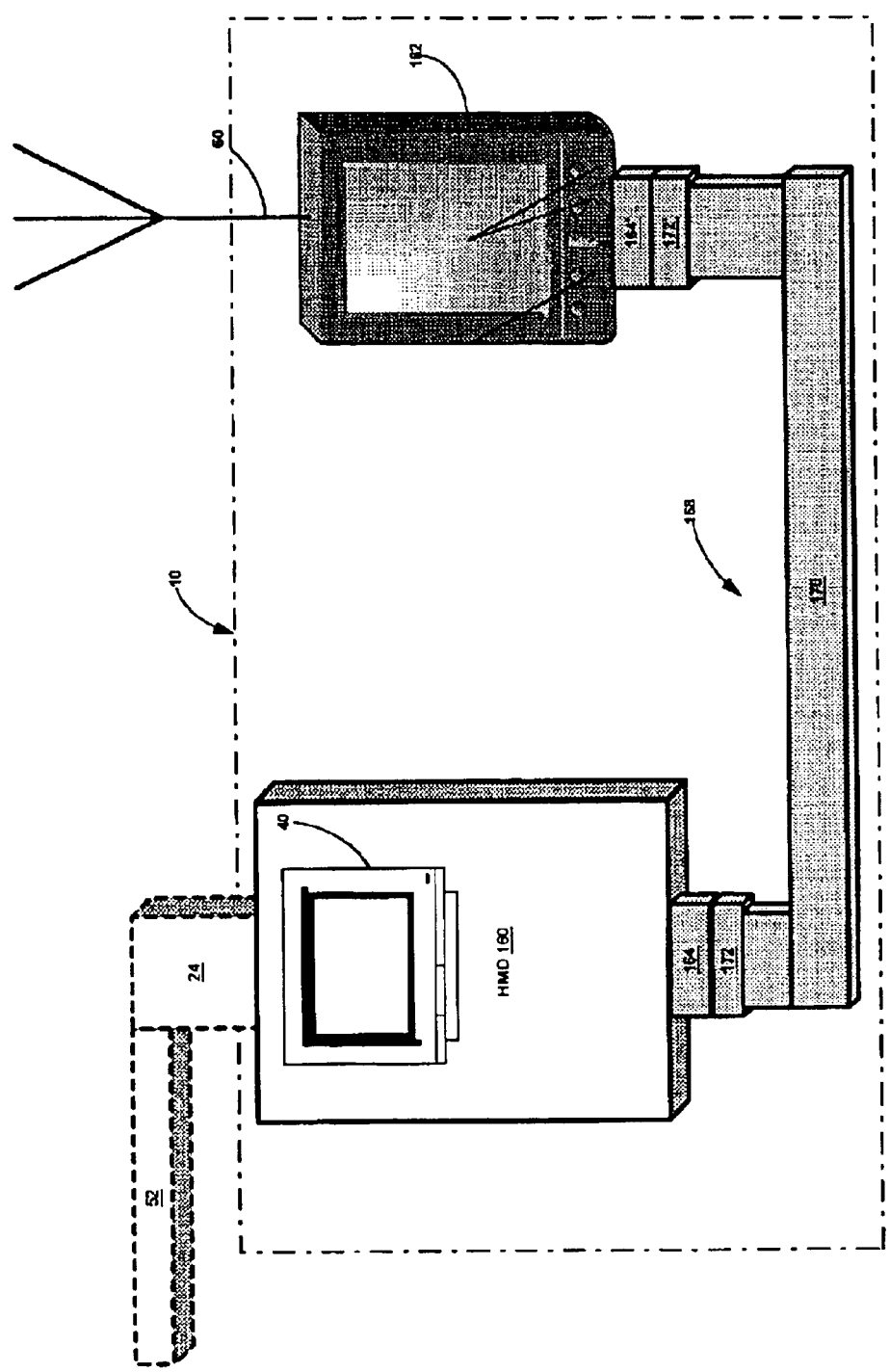
FIG. 7 illustrates an embodiment of a wired connection between a HMD and a WWD, also showing an optional adaptor.

Referring to FIG. 7, an embodiment of the connection is shown. In this figure, a hardware (or "wired") connection is shown, i.e., an adaptor 168, disposed between a HMD 160 and a WWD 162. In most circumstances, it is assumed that the varieties of HMDs will vary more widely than the varieties of WWDs. Accordingly, HMD 160 will likely have one of a variety of types of connectors for input/output purposes, here shown as a connector 164. Connector 164 mates with a connector 172 of adaptor 168. At another point on adaptor 168 is a connector 172' for connecting to a generic input/output port 164' on WWD 162. A cable 170 is disposed between the two connectors, cable 170 capable of including adaptor circuitry if desired.

Of course, the use and structure of adaptor 168, between HMD 160 and WWD 162, depends on factors such as the prevalence of an industry standard for such communications. In other words, if the output of HMD 160 is readily acceptable to WWD 162, then the same may be directly connected or may be connected via a simple cable, the same basically extending from pin-to-pin. For example, a standard parallel bus or serial cable may be used if the input/output ports between the HMD and the WWD, which may be, e.g., RS232, are compatible. Otherwise, a suitable adaptor circuit as noted above may be employed. The connection may also be an input such as a disk drive or other media input for input of data, a USB port or phone jack or other such wired input, again employing an adaptor circuit if required.

Port 164' can be used to communicate with HMD 160 and connector 164 via a number of types of wired connections, including USB, USB2 or Firewire. In some cases, optional adaptor 168 may also be employed.

A connection may simply be made by providing optional adaptor 168 with adaptor circuitry, such as within cable 170 or within a circuit box therein, so as to match up the appropriate or complementary pins.

In other embodiments, such as for devices connected to proprietary connectors, a less standard and perhaps proprietary pin-out may be required.

Figure 8:
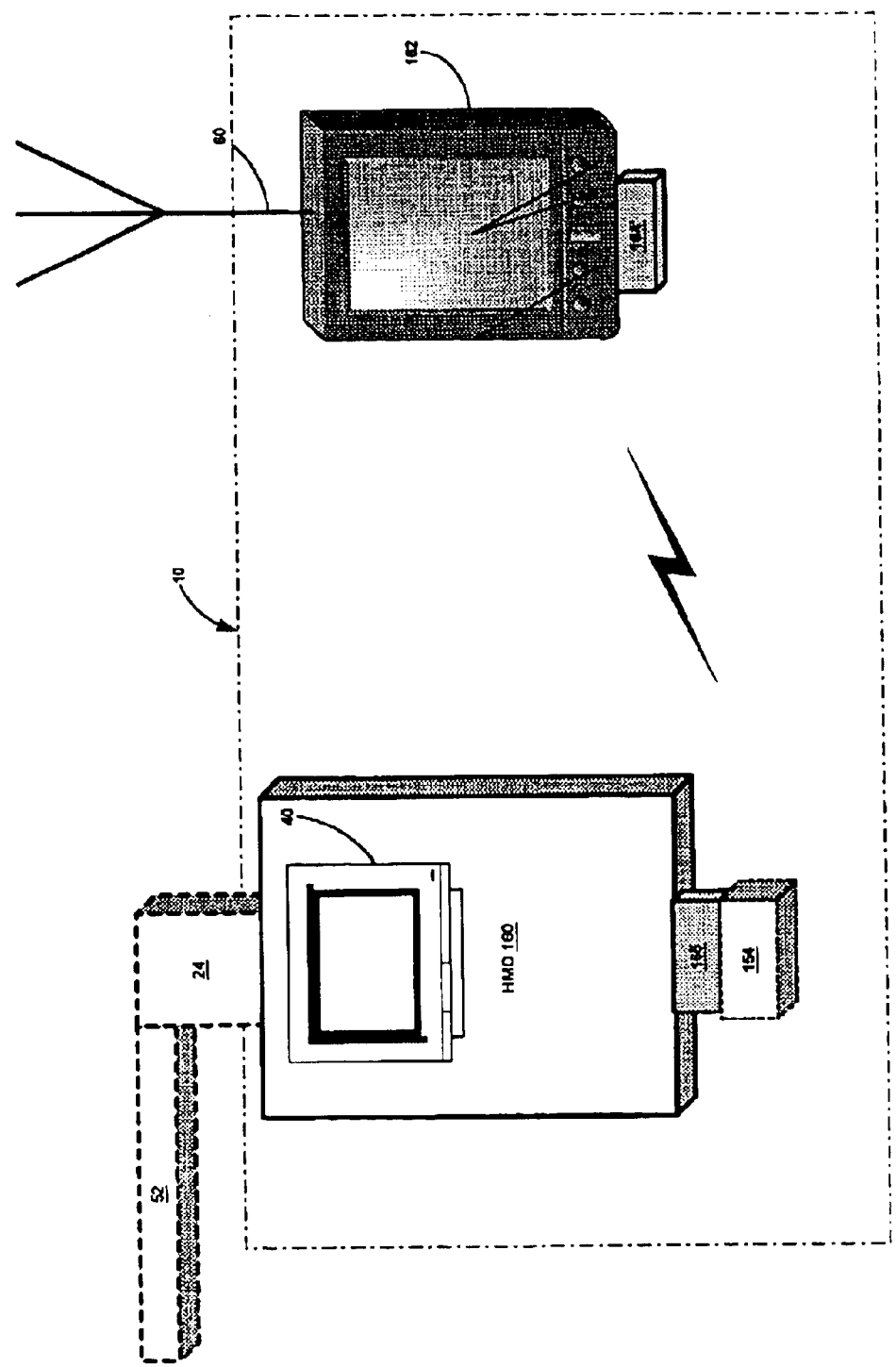
FIG. 8 illustrates an embodiment of a wireless connection between a HMD and a WWD, also showing an optional adaptor.

Referring to FIG. 8, an embodiment of a wireless implementation of the WHMA 10 is shown. In FIG. 8, a wireless connection is shown between HMD 160 and WWD 162. HMD 160 may have an integral wireless modulator/demodulator disposed within (not shown). More likely, however, is that HMD 160 has an adaptor 165 connectable thereto which performs these functions. WWD 162 may have an integral wireless modulator/demodulator (not shown), although an adaptor can also be used in this context.

While the device shown in FIG. 8 is described in the context of general wireless communications, various protocols may be employed. For radio frequency communications, protocols such as Bluetooth® or 802.11 may be advantageously employed. Other techniques employing a similar configuration include those employing IR, microwaves, optical techniques including lasers, and so on.

It should be understood that the above is merely exemplary, and that the form of the adaptor may vary widely between HMDs and WWDs.

The above description of a remote health monitoring system, termed occasionally a "telemedicine" system, clearly provides a valuable tool for the remote diagnosis and management of patients.

Besides the patient data transmission from HMDs, other sorts of transmissions may also occur. For example, visual data, such as photographs or videos, may be transferred as an indication of the patient's condition and to aid remote diagnosis. Alternatively, other visual indications of a patient's status, such as graphical or other outputs of HMDs, may provide information useful for a diagnosing/treating physician.

In these embodiments, a set of visual data from a camera or from an HMD may be transmitted from the WWD to a wireless antenna that is connected to the wired telecommunications infrastructure. Overlaid on this is the internet, and the visual data may thus be sent via an appropriate protocol to a server for retrieval and analysis by a user such as a treating 'off-site' physician.

U.S. Pat. No. 5,441,047 describes a system by which images and data may be transmitted by standard telephone lines or wireless telemetry systems. Systems also allow for such transfers over wireless or cellular systems, e.g., U.S. Pat. No. 5,987,519. Moreover, the advent of cellular phones and WWDs that include a digital camera (or alternatively are equipped with a link to one) allow the capture and transmission of photographic images using low-cost consumer devices. In this way, transmission of information may be particularly convenient and may occur when a regular telephone connection is unavailable, such as in a medical emergency, in a rural setting, or during transportation of a patient.

In such systems, an additional security layer may be employed, including industry-standard encryption and decription of the transmitted data, especially as patient health information is highly sensitive and private data.

Despite the obvious advantages of cellular or mobile systems, disadvantages also inure. For example, interruptions of service, "drop-outs", may occur between cells and in many locations service is not available.

Moreover, current WWDs often lack sufficient on-board memory for storage of visual data, such as from cameras or data-intensive HMDs.

Figure 9:
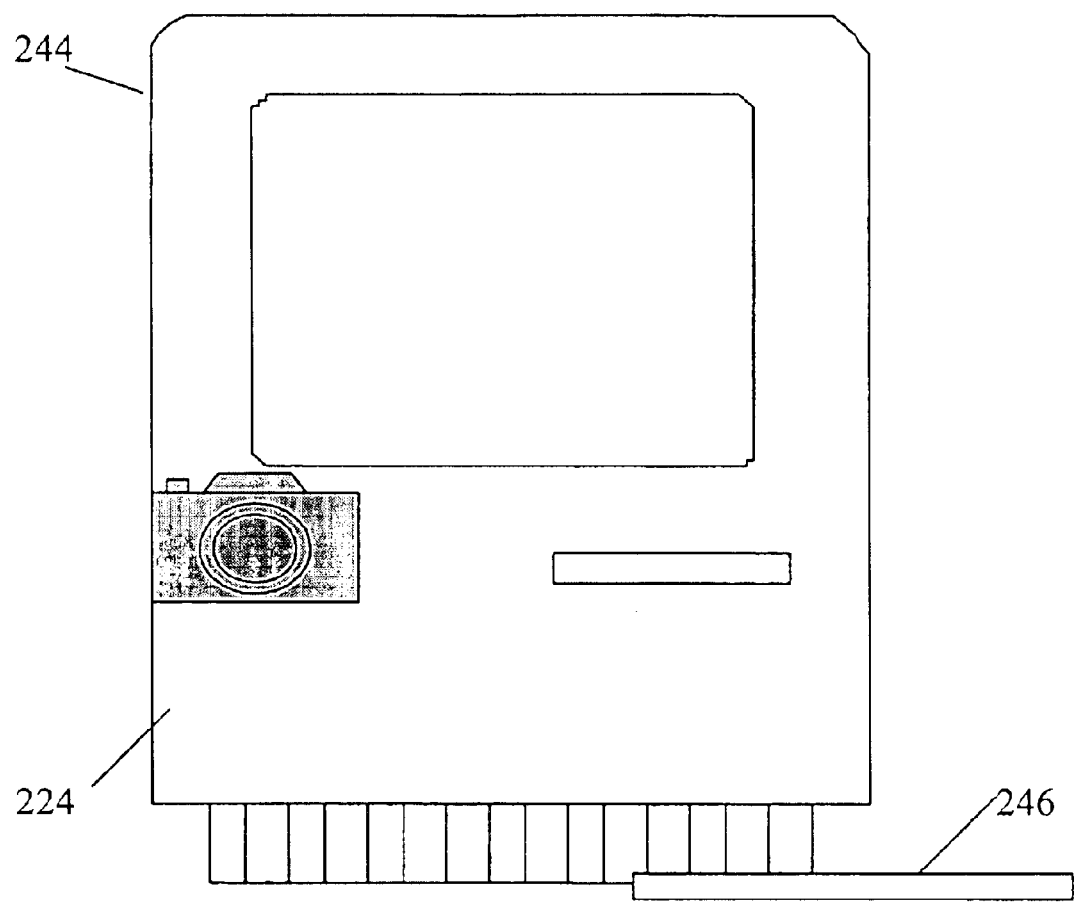
FIG. 9 illustrates an embodiment of a wireless system for transmitting visual data to and from a user.

Embodiments of the present invention at least in part assists in such cases. Referring to FIG. 9, a system is shown in which a WWD 244 is shown with a memory device 246. The memory device 246 may be a smartcard, a smartmedia card, a memory card, memory stick, compact flash card, memory cubes, micro-drives, disk-on-keys, flash memory-keys, micro-laser disks, nano-storage devices, bio-memories, battery/memory combination device, USB flash drives, and so on, or indeed any other type of removable media that may be connected to a WWD to store information. Typically, these memory devices are capable of storing substantial amounts of data. The same may also include a memory and power source or combination device.

Figure 10:
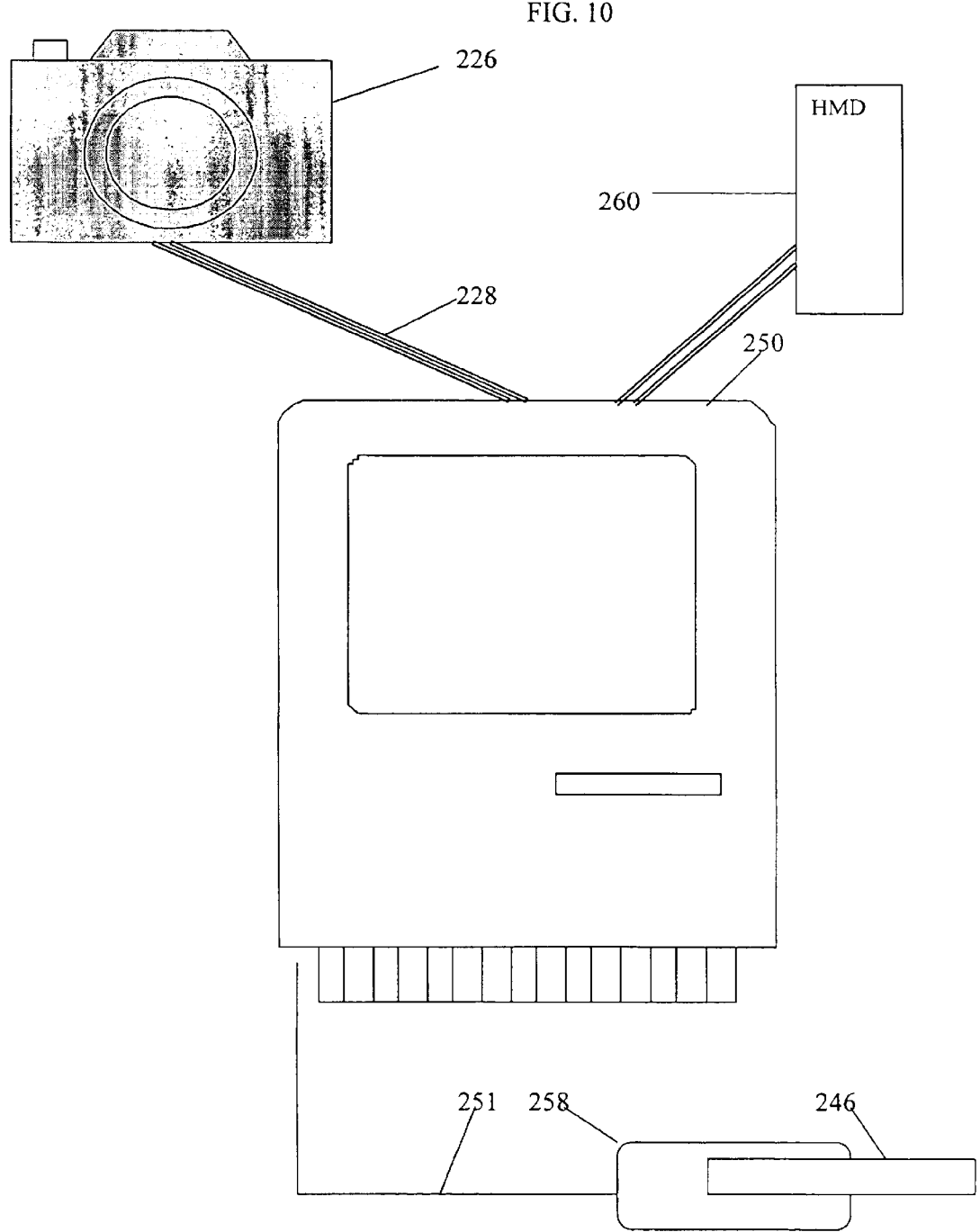
FIG. 10 illustrates an alternative embodiment of a wireless system for transmitting visual data to and from a user.

In another embodiment, shown in FIG. 10, the memory device 246 is shown inserted in a memory device reader 258, which is in turn connected to a WWD 250 via link 251.

The memory device 246 then allows for enhanced functionality of the WWDs 244 or 250. In one respect, they allow for increased data storage. This may be particularly important for medical data, as certain health monitoring apparatuses produce copious amounts of data, e.g., cardiac monitoring equipment, and thus require substantial storage capabilities.

Another reason such memory devices are particularly pertinent in medical device monitoring is that they store data which can then be wirelessly transmitted in a streamed or non-streamed fashion. In the event of drop-outs, interruptions, or unavailability, of the wireless network, no loss of data occurs, as the data has been stored on the memory device and may be wirelessly transmitted at a later time when cellular or mobile service is again available. The memory device thus serves as a back-up storage media. In the event of an extended period of unavailability of a wireless network, the memory device may be replaced or overwritten to provide practically unlimited storage until such time as the network is available and the data can be uploaded.

Of course, even if the wireless network is available, the memory device or on-board WWD memory may store the data for various purposes. This real-time capability and robustness is often very important in ensuring patient safety and ensuring that a high level of care is being delivered to the patient by the caregiver, particularly in field or emergent situations where the wireless connection may be the only source of communications with a physician.

A related reason why memory devices are particularly pertinent in medical device monitoring is that they allow a greater level of buffering for real-time data monitoring, thus allowing more pre-analysis and filtering of data.

Figure 12:
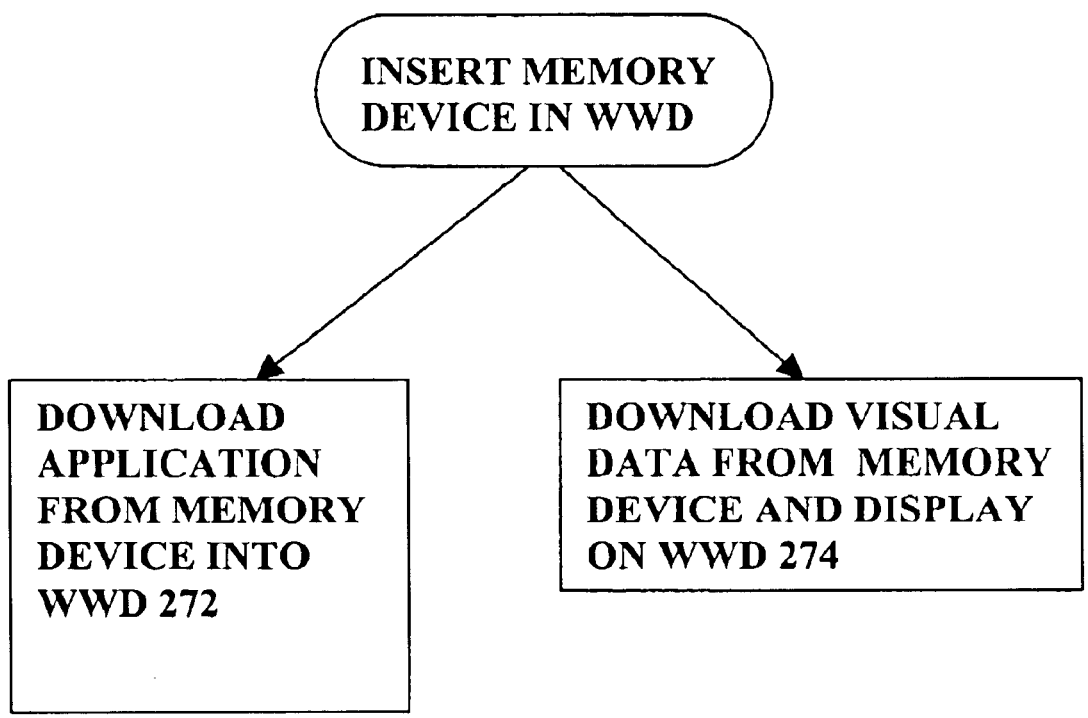
FIG. 12 illustrates an embodiment of a method for using a memory device to load an application program onto a wireless system.

A further benefit of the use of memory devices is that they provide for easy application downloading (step 272 of FIG. 12) onto a WWD. For example, a memory device may be inserted into a WWD (step 270 of FIG. 12) and a large application program may be easily downloaded onto a WWD from the memory device rather than through a wired or wireless synchronization or downloading process via a PC or the internet or both. Downloading in this fashion may be particularly rapid and complete. The downloaded data may include visual data (step 274 of FIG. 12), such as still or video photographic images, that instruct a user on the operation of a device. In an alternative embodiment, the data need not be downloaded but may rather be streamed, either from a stored video on a server or in real-time via a user with a webcam. In downloaded or streamed by generally not live systems, the user interface may be interactive, allowing the user to access a knowledge database resident on the server or memory device or previously downloaded onto the main memory of the WWD.

Particularly important types of data about a patient that presents with a malady (step 202 of FIG. 11) that may be wirelessly transmitted from the WWD are those corresponding to photographic pictures, both still and video, and graphical or visual data output images from an HMD, e.g., an ECG output. In either case, medical personnel may arrive on an emergent scene and engage the WWD (step 204 of FIG. 11). Some action may be taken immediately if warranted (step 206 of FIG. 11).

To obtain the first type of data noted above, photographic data, a camera may be employed, which is either resident on the WWD (camera 224 of FIG. 9) or is otherwise available by way of a link 228 (camera 226 of FIG. 10). The WWD 250 may store photographic data, either still or video, and transmit the same wirelessly to a point of collection, e.g., a server application, or may save the photographic data on the memory device for contemporaneous or later transmission, again either via a streamed, non-streamed, or other transmission method (step 208 of FIG. 11).

To devise the second type of data mentioned above, a data port from a HMD 260 that is coupled to a patient (step 210 of FIG. 11) may be employed to send information from the same to an input port on the WWD 250. This transmission may be accomplished via the techniques described above. Such data may be in either a raw form or in a preformatted-for-video form, and may be stored in the WWD or on the memory device (step 212 of FIG. 11). In either case, it may be required to format the data in a way suitable for the display screen of the WWD. In some cases, viewing on the WWD is not necessary, and the data may be sent in its original form, optionally undergoing some intermediate processing, directly on to the off-site caregiver's system for viewing or analysis (step 214 of FIG. 11). Examples of this type of data may be ECG data, such as from an ECG recorder or from the ECG output port of an emergency portable defibrillator, or other sources of data. Alternatively, a subset of the data may be sent, such as a compressed version, while the remainder, i.e., the complete version of the patient data, may be maintained on the WWD and/or memory device for purposes of maintaining a complete patient record.

As above, the WWD may store the HMD data, and transmit the same wirelessly to a point of collection or may save the data on the memory device for contemporaneous or later transmission, again either via a streamed or other transmission method.

Figure 11:
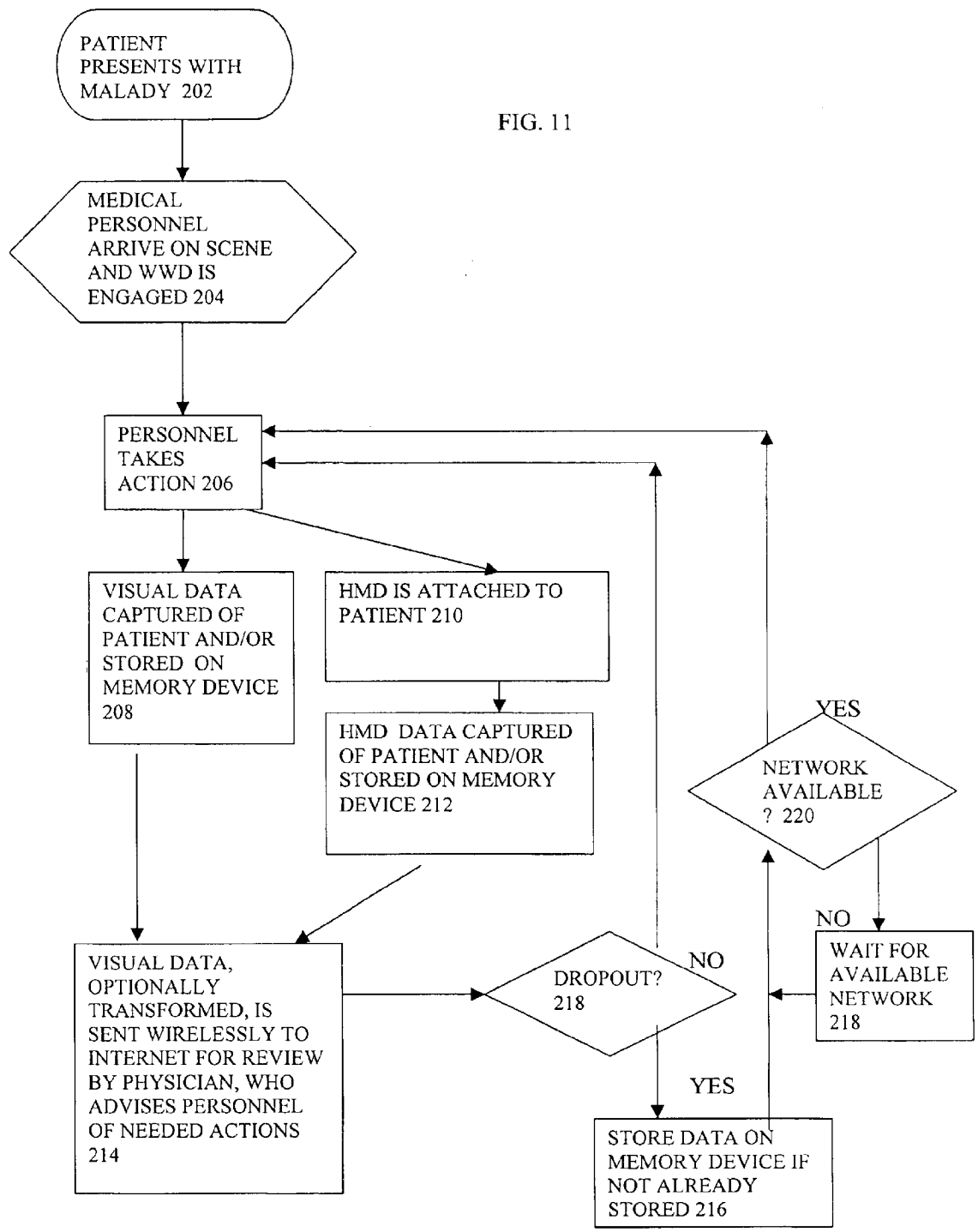
FIG. 11 illustrates an embodiment of a method for using a wireless system to transmit visual data to and from a user.

In more detail, in the case of a dropout or other disruption of wireless service (step 218 of FIG. 11), the data may be stored on the memory device or in the WWD if it has not already been, as may be the case for streamed data (step 216 of FIG. 11). The WWD may periodically test for the availability of the wireless network (step 220 of FIG. 11), and may wait until the network is available (step 218 of FIG. 11). Once the system is again available, the advice from the caregiver may be sent to the WWD and the on-site personnel may again take action (step 206 of FIG. 11).

Using such data, an off-site health care professional may give an on-site caregiver valuable diagnosis and treatment advice. Moreover, no wired or dedicated connection is necessary. In addition, the above-noted difficulties with wireless or cellular systems may be overcome.

There are various ways in which visual data may be communicated to an off-site caregiver. A simple method is to send the visual data via an email message. In more advanced methods, the visual data may be integrated with a data stream of other medical information. Current systems may be used in combination with the present invention to facilitate the handling and transmission of visual data by a WWD. For example, current operating systems for WWDs include Windows Mobile, Symbian; current application programming languages include Java; current software libraries and development environments include MobilityWorld. In all cases, the visual data may be stored, e.g., as a separate file or may be included as an embedded object in a data file on the memory device or in an email.

It will be understood that the above description of a "Method and Apparatus for Health and Disease Management Combining Patient Data Monitoring with Wireless Internet Connectivity" has been with respect to particular embodiments of the invention. While this description is fully capable of attaining the objects of the invention, it is understood that the same is merely representative of the broad scope of the invention envisioned, and that numerous variations of the above embodiments may be known or may become known or are obvious or may become obvious to one of ordinary skill in the art, and these variations are fully within the broad scope of the invention. For example, while certain wireless technologies have been described herein, other such wireless technologies may also be employed. Furthermore, while various types of medical devices have been mentioned, numerous other types may also be used in the embodiments of the invention, including pulse oximeters, implanted monitors, syringe drivers, infusion pumps, spirometers, ventilators, anesthesia monitors, blood glucose meters, and so on. Accordingly, the scope of the invention is to be limited only by the claims appended hereto, and equivalents thereof. In these claims, a reference to an element in the singular is not intended to mean "one and only one" unless explicitly stated. Rather, the same is intended to mean "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present invention is intended to be dedicated to the public regardless of whether the element, component, or method step is explicitly recited in the claims. No claim element herein is to be construed under the provisions of 35 U.S.C. §§112, ¶6, unless the element is expressly recited using the phrase "means for".

What is claimed is:

1. A wireless health-monitoring system for monitoring a disease state or condition of a patient using visual data, comprising:
    an internet-enabled wireless web device including an integral digital camera, a communications port having a circuit for wireless communications with a network, a memory device, and a user interface;
    a server application, residing on a computer readable medium and disposed on a server in communication with the wireless network, for causing the server to:
    receive visual data from the digital camera; and
    display the visual data,
    wherein in the event of an interruption of a wireless connection between the internet-enabled wireless web device and the wireless network, the internet-enabled wireless web device is configured to store the visual data from the digital camera in a memory or on the memory device.

2. The system of claim 1, wherein the internet-enabled wireless web device is selected from the group consisting of: an internet-enabled mobile phone; a handheld, palm, or laptop computer or personal digital assistant having an optional implemented or integral wireless capability; and a hybrid device of a handheld computer and mobile telephone.

3. The system of claim 1, further comprising:
    a memory device removably insertable into the internet-enabled wireless web device including an application program capable of being run from the memory device or run subsequent to download into the memory of the internet-enabled wireless web device.

4. The system of claim 3, wherein the application program includes instructional materials, or visual still or video images.

5. A wireless health-monitoring system for monitoring a disease state or condition of a patient using visual data from a health-monitoring device, comprising:
    an internet-enabled wireless web device including a generic input/output port for reception of visual data from an output port of a health-monitoring device, a circuit for wireless communications with a network, a memory device, and memory configured to store:
        visual data corresponding to a health parameter, the health parameter corresponding to a disease state or condition of a patient and determined by the health monitoring device:
        a device application; and
        a user interface; and
    a server application, residing on a computer readable medium and disposed on a server in communication with the wireless network, for causing the server to:
    receive the visual data; and
    display the visual data.

6. The system of claim 5, wherein in the event of an interruption of a wireless connection between the internet-enabled wireless web device and the wireless network, the internet-enabled wireless web device is configured to store the visual data from the health-monitoring device in the memory or on the memory device.

7. A method of wirelessly monitoring the disease state or condition of a patient via viewing photographic data corresponding to the patient, comprising:
    capturing a visual image of a patient via a camera, the camera integral with or connected via a link to an internet-enabled wireless web device having a memory device;
    wirelessly transmitting the visual image to a server via a wireless network;
    receiving the visual image at the server;
    wherein if the wireless transmitting between the internet-enabled wireless web device and the wireless network is interrupted, further comprising storing the photographic image on the memory device or in a memory of the internet-enabled wireless web device.

8. The method of claim 7, where the image is a video image, a still image, a streamed image, or a non-streamed image.

9. The method of claim 7, further comprising:
    Attaching a memory device to the internet-enabled wireless web device including an application program, and running the application program from the memory device or from the memory or subsequent to download of the application program into the memory.

10. The method of claim 9, whereby the application program includes instructional materials, photographic still or video images.

11. A method of wirelessly monitoring the disease state or condition of a patient using visual data from a health monitoring device, comprising:
    transmitting visual data from a health monitoring device corresponding to a health parameter to an internet-enabled wireless web device having a memory device via a port, the health parameter corresponding to a disease state or condition of a patient;
    wirelessly transmitting the visual data to a server;
    receiving the visual data at the server;
    displaying the visual data; and
    wherein in the event of an interruption of a wireless connection between the internet-enabled wireless web device and the wireless network, the internet-enabled wireless web device is configured to store the visual data from the health monitoring device in a memory or on the memory device.

12. The method of claim 11, further comprising:
    Attaching a memory device to the internet-enabled wireless web device, the memory device including an application program, and running the application program from the memory device or from the memory subsequent to download of the application program into the memory.

13. The method of claim 12, whereby the application program includes instructional materials, or photographic still or video images.

14. A computer program, residing on a computer-readable medium, containing instructions for causing an internet-enabled wireless web device in signal communication via a wireless network to the internet to:
   cause an internet-enabled wireless web device to receive data corresponding to a visual image of a patient from a camera connected to or integral therewith, the visual data indicative of a disease state or condition of a patient;
   wherein in the event of an interruption of the wireless connection between the internet-enabled wireless web device and the wireless network, the internet-enabled wireless web device is configured to store the visual data from the camera in a memory or on a removable memory device.

15. A computer program, residing on a computer-readable medium, containing instructions for causing an internet-enabled wireless web device in signal communication via a wireless network to the internet to:
   cause an internet-enabled wireless web device to receive via data corresponding to a health parameter of a patient from a health monitoring device connected to or integral with the internet-enabled wireless web device, the health parameter indicative of a disease state or condition of a patient;
   wherein in the event of an interruption of the wireless connection between the internet-enabled wireless web device and the wireless network, the internet-enabled wireless web device is configured to store the health parameter from the health monitoring device in a memory or on a removable memory device.

16. A internet-enabled wireless web device for monitoring health, the internet-enabled wireless web device connected in wireless communication with a server running an application, comprising:
   an internet-enabled wireless web device with a removable memory device and running an application, the application functioning to accept inputs from a first communications port and a second communications port, the first communications port including a generic input/output port and the second communications port including a wireless link to a network, the generic input/output port for receipt of a health parameter from a health monitoring device or visual data from a digital camera, the health parameter or visual data corresponding to a patient's disease state or condition;
   wherein in the event of an interruption of the wireless connection between the internet-enabled wireless web device and the server, the internet-enabled wireless web device is configured to store the health parameter or visual data in a memory or on the removable memory device.

17. The system of claim 16, wherein the internet-enabled wireless web device is selected from the group consisting of: an internet-enabled mobile phone; a handheld, palm, or laptop computer or personal digital assistant having an optional implemented or integral wireless capability; and a hybrid device of a handheld computer and mobile telephone.

* * * * *

UNITED STATES PATENT AND TRADEMARK OFFICE
CERTIFICATE OF CORRECTION

| | |
|---|---|
| PATENT NO. | : 6,976,958 B2 |
| APPLICATION NO. | : 10/773501 |
| DATED | : December 20, 2005 |
| INVENTOR(S) | : Roger J. Quy |

It is certified that error appears in the above-identified patent and that said Letters Patent is hereby corrected as shown below:

On the title page item (57)
Abstract,
Line 13, change "handing" to - - handling - - .

Column 1
Line 42, after "approach", change "had" to - - has - - .
Line 43, after "prevalent" change "is" to - - in - - .

Column 2
Line 2, change "location" to - - locations - -.
Line 55, before "data", change "provided" to - - provide - -.

Column 3
Line 30, after "maintain", insert - - a - - .

Column 4
Line 26, change last word "user" to - - user's - - .
Line 48, after "system," change "rules based" to - - rules-based - - .

Column 5
Line 65, after "monitor," change "include" to - - including - -.

Column 6
Line 29, after "type of", change "convention" to - - conventional - - .
Line 45, after "FIG. 2," change "an" to - - a - -.

Column 8
Line 30, after "storage", insert - - device - - .

Column 9
Line 52, after "generally", insert - -, and - - .
Line 64, change "interact" (second occurrence) to - - interaction - - .

Column 10
Line 31, change "termed" to - - term - -.

Column 12
Line 51, change first word "assists" to - - assist - - .

UNITED STATES PATENT AND TRADEMARK OFFICE
CERTIFICATE OF CORRECTION

PATENT NO. : 6,976,958 B2
APPLICATION NO. : 10/773501
DATED : December 20, 2005
INVENTOR(S) : Roger J. Quy It is certified that error appears in the above-identified patent and that said Letters Patent is hereby corrected as shown below:

Column 13
Line 10, after "unavailability", delete - - , - - .

Column 14
Line 46, change "Windows Mobile" to - - Windows Mobile® - -.
Line 46, change "Symbian" to - - Symbian® - - .
Line 47, change "Java" to - - Java® - -.
Line 48, change "MobilityWorld" to - - MobilityWorld™ - -.
Line 54, between "been" and "with", insert - - described - -.
Line 60, after "known", insert - - , - - .
Line 60, after "obvious" (second occurrence), insert - - , - - .

Claims
Claim 15, line 24, delete first word - - via - -.

Signed and Sealed this

Eighth Day of August, 2006

JON W. DUDAS
*Director of the United States Patent and Trademark Office*

Disclaimer

6,976,958 B2 - Roger J. Quy, Mill Valley, CA (US). METHOD AND APPRATUS FOR HEALTH AND DISEASE MANAGEMENT COMBINING PATIENT DATA MONITORING WITH WIRELESS INTERNET CONNECTIVITY. Patent dated December 20, 2005. Disclaimer filed August 10, 2020, by the assignee Philips North America LLC.

Hereby enters this disclaimer to the complete claims 15, 16 and 17 of said patent.

*(Official Gazette, May 25, 2021)*